US010126231B2

(12) United States Patent
Villa-Aleman et al.

(10) Patent No.: US 10,126,231 B2
(45) Date of Patent: Nov. 13, 2018

(54) HIGH SPEED SPECTROSCOPY USING TEMPORAL POSITIONED OPTICAL FIBERS WITH AN OPTICAL SCANNER MIRROR (71) Applicant: Savannah River Nuclear Solutions, LLC, Aiken, SC (US)

(72) Inventors: Eliel Villa-Aleman, Aiken, SC (US); William A. Spencer, Aiken, SC (US)

(73) Assignee: Savannah River Nuclear Solutions, LLC, Aiken, SC (US)

(*) Notice: Subject to any disclaimer, the term of this patent is extended or adjusted under 35 U.S.C. 154(b) by 0 days.

(21) Appl. No.: 15/459,209

(22) Filed: Mar. 15, 2017

(65) Prior Publication Data

US 2018/0266940 A1    Sep. 20, 2018

(51) Int. Cl.
G01J 3/30 (2006.01)
G01N 21/25 (2006.01)
G01N 21/71 (2006.01)
G01N 21/27 (2006.01)
G02B 6/32 (2006.01)
G02B 26/12 (2006.01)

(52) U.S. Cl.
CPC ......... G01N 21/255 (2013.01); G01N 21/27 (2013.01); G01N 21/718 (2013.01); G02B 6/32 (2013.01); *G01N 2201/0833* (2013.01); *G01N 2201/105* (2013.01); *G02B 26/12* (2013.01)

(58) Field of Classification Search
CPC ...... G01N 21/25; G01N 21/255; G01N 21/27; G01N 21/71; G01N 21/68; G01N 21/73; G02B 6/32; G01J 3/44
See application file for complete search history.

(56) References Cited

U.S. PATENT DOCUMENTS

| 4,548,790 A | 10/1985 | Horwitz et al. |
| 5,371,358 A | 12/1994 | Chang et al. |
| 5,373,093 A | 12/1994 | Vallarino et al. |

(Continued)

FOREIGN PATENT DOCUMENTS

| WO | WO 2014/060118 | 4/2014 |
| WO | WO 2015/061013 | 4/2015 |

OTHER PUBLICATIONS

NCBI / L. et al. "A Combined Experimental and Theoretical Study on the Extraction of Uranium by Ameno-Derived Metal-Organic Frameworks Through Post-Synthetic Strategy" Dated Nov. 16, 2016 (2 pages).

(Continued)

*Primary Examiner* — Abdullahi Nur
(74) *Attorney, Agent, or Firm* — Dority & Manning, P.A.

(57) ABSTRACT

Systems and methods for examining spectral data over the course of a high speed event are described. The systems and methods can enable observation of the spectral evolution of a transient phenomenon into segment intervals on the order of, milliseconds or microseconds. The methods include reflecting light from an event off of a rotating mirror and sequentially delivering light from the mirror to a series of optical waveguides for sequential spectral analysis. The systems and methods can be useful in a wide variety of applications such as, LIBS applications; examination of high energy devices such as explosions or simulations of explosions; examination of deposition processes, e.g., coating formations; examination of chemical reactions; etc.

16 Claims, 4 Drawing Sheets

(56) References Cited

U.S. PATENT DOCUMENTS

| | | | |
|---|---|---|---|
| 6,060,677 | A | 5/2000 | Ulrichsen et al. |
| 6,421,164 | B2 | 7/2002 | Tearney et al. |
| 6,943,892 | B2 | 9/2005 | Chan |
| 7,006,765 | B2 | 2/2006 | Hendow |
| 7,010,336 | B2 | 3/2006 | Lorenz et al. |
| 7,041,959 | B1 | 5/2006 | Palme et al. |
| 7,248,358 | B2 | 7/2007 | Geshwind et al. |
| 7,251,028 | B2 | 7/2007 | Carver |
| 7,456,021 | B2 | 11/2008 | Brant et al. |
| 7,799,293 | B2 | 9/2010 | Peterman et al. |
| 7,854,907 | B2 | 12/2010 | Gong et al. |
| 8,259,298 | B2 | 9/2012 | Berghmans |
| 8,645,082 | B2 | 2/2014 | Tan et al. |
| 8,916,692 | B2 | 12/2014 | Leif et al. |
| 8,982,357 | B2 | 3/2015 | Yoshida et al. |
| 9,113,023 | B2 | 8/2015 | Bridges et al. |
| 9,155,474 | B2 | 10/2015 | Carver et al. |
| 9,267,896 | B2 | 2/2016 | Cha et al. |
| 9,511,346 | B2 | 12/2016 | Tour et al. |
| 9,696,426 | B2 * | 7/2017 | Zuk .................. G01S 17/107 |
| 2004/0064259 | A1 | 4/2004 | Haaland et al. |
| 2006/0132778 | A1 * | 6/2006 | Curry ................ G01N 15/1468 356/417 |
| 2006/0167350 | A1 | 7/2006 | Monfre et al. |
| 2007/0252978 | A1 | 11/2007 | Van Der Voort et al. |
| 2008/0034025 | A1 | 2/2008 | Zubkov et al. |
| 2008/0248583 | A1 | 10/2008 | Ericson et al. |
| 2010/0219344 | A1 | 9/2010 | Duckworth et al. |
| 2016/0025872 | A1 | 1/2016 | Taleyarkhan |
| 2016/0042825 | A1 | 2/2016 | Shilova et al. |
| 2016/0062112 | A1 | 3/2016 | Potsaid et al. |
| 2016/0213252 | A1 | 7/2016 | Hillman et al. |

OTHER PUBLICATIONS

ACS Publications / Selvan Demirtt "Extraction of Lanthanide and Actinide Ions from Aqueous Mixtures Using a Carboxylic Acid-Functionalized Porous Aromatic Framework" Dated 2017 (2 pages).

Optic Letters / Linbo Liu et al. "Double-Reflection Polygon Mirror for High Speed Optical Coherence Microscopy" Dated Dec. 15, 2007 (3 pages).

Optic Letters / Wibool Piyawattanametha "Fast-Scanning Two-Photon Fluroescence Imaging Based on a Microelectromechanical Systems Two-Dimensional Scanning Mirror" Dated Jul. 1, 2006 (3 pages).

Optic Letters / Nan Guang et al. "Rotary Mirror Array for High-Speed Optical Coherence Tomography" Dated Apr. 15, 2002 (3 pages).

OSA Publishing / Youxin Mao "Simultaneous Dual-Wavelength-Band Common Path Swept-Source Opitcal Coherence Tomography with Single Polygon Mirror Scanner" Dated 1990-1992 (4 pages).

Polygonal Laser Scanners, Fitting the Elements to the Task/Glenn E. Stutz, Lincoln Laser Co. Aug. 1, 2008 vol. 33, No. 15/Optics Letters 1741.

High-Speed Polygon-Scanner-Based Wavelength-Swept Laser Source in the Telescope-Less Configuration with Application in Optical Coherence Tomography / S. M. R. Motaghian Nezam. Optics Letters vol. 33, Issue 15, pp. 1741-1743 (2008).

A Book Chapter (pp. 475-483) From New Trends in Mechanism Science and Machine Science /V.F. Duma, J.P. Rolland vol. 5, 2010 Jul. 27, 2010, Mechanical Constraints and Design Considerations for Polygon Scanners.

* cited by examiner

HIGH SPEED SPECTROSCOPY USING TEMPORAL POSITIONED OPTICAL FIBERS WITH AN OPTICAL SCANNER MIRROR

STATEMENT REGARDING FEDERALLY SPONSORED RESEARCH OR DEVELOPMENT

This invention was made with government support under Grant No. DE-AC09-08SR22470 awarded by the U.S. Department of Energy. The government has certain rights in the invention.

BACKGROUND

Spectrophotometers are useful in many detection regimes as they can effectively measure the result of light-matter interaction at multiple wavelengths. The interaction can take the form of absorbance as light is transmitted through a sample, changes to the light as it is scattered from a sample, or emission of light as a result of an interaction. By measuring a response at multiple wavelengths, spectrophotometers can acquire a great deal of information that can be used to distinguish various sources of signal changes, e.g., multiple analytes. These capabilities allow the spectrophotometer to be used in situations where the properties of the sample may be changing over time, e.g. as a monitor for a particular analyte in a chemical process. As a result of such capabilities the accuracy of analyte detection and measurement with spectrophotometers can be higher than with other detection approaches.

Unfortunately, spectral analysis is limited to a single snapshot of a sample or event at the particular time of detection. For instance, in order to monitor an analyte in a chemical process, a plurality of samples will generally be collected over the time period of interest, with each sample then separately analyzed. While such a single-shot approach is highly effective in many situations, it will not work for temporal examination of a high speed event. For example, during laser-induced breakdown spectroscopy (LIBS), a laser is focused to form a plasma that is then used to ablate and excite a sample. LIBS is often used to evaluate the presence or abundance of constituent elements in a sample, but in practice, detection is limited to a very small light collection window and as such a temporally gated detector is utilized. If this window is mistimed the results of the detection protocol can be inaccurate. Moreover, a laser-induced plasma can emit a continuum of radiation over a time period on the order of microseconds or milliseconds, and the spectral analysis capability of current systems cannot provide information with regard to changes in the spectral activity of the system over the course of the entire time period. Use of time gated detectors has provided one route for temporal characterization, but this approach calls for repetition of an experiment with each repetition using a set of different time gates. Unfortunately however, some events cannot be easily repeated.

Another example of a transitory system for which high speed temporal spectroscopy would be useful is in the study of detonation of high energy devices in which the temporal formation of particulates and the correlation with radiant emissions are not well understood. Spectral emission from elemental and molecular species during high energy device detonations (or simulations thereof) can be used to better understand the activities and changes of materials under high temperatures and pressures. Since spectral information is highly dependent on temporal behavior over the course of such a high speed event, it would be highly beneficial to investigate the variation of spectra on the temporal scale of a detonation.

What are needed in the art are optical measurement systems and methodologies that can be used to examine a system over the course of a high speed event, for instance an event measured on the order of milliseconds or less.

SUMMARY

According to one embodiment, disclosed is a spectroscopy system that includes a rotatable mirror configured for location in optical communication with an event, e.g., a high speed event such as formation of a plasma. A system can also include a plurality of optical waveguides, e.g., optical fibers, and each of these waveguides can include a collection lens on one end. This end of each of the waveguides (i.e., the end with the collection lens) can be in optical communication with the rotatable mirror. The system can also include a spectrophotometer that includes one or more detectors (e.g., spectrometers) in optical communication with the second end of the optical waveguides.

Also disclosed is a method for examining a high speed event that can include locating the rotatable mirror in optical communication with the event. Beneficially, the use of the rotatable mirror allows a temporal event (e.g., a high speed event) to be transformed to a spatial distance. Light from a first time period during the event (e.g., on the order of a few microseconds or less) can be reflected by the mirror to a collecting lens of a first optical waveguide. Following rotation of the mirror, light from a second time period during the event can be reflected by the mirror to a collecting lens of a second optical waveguide, and so on for additional time periods and additional fibers over the course of an entire time period of interest. The rotational rate of the mirror can be controlled so as to allow the temporal window of the analysis to be adjusted.

The method can also include carrying out a spectral analysis of the light collected by each waveguide from each time period. Thus, a plurality of spectral analyses can be provided that can include temporal and spectral information over the entire course of the time period of interest. Beneficially, the spectral analyses can be carried out according to any suitable methodology and with any desired spectrophotometer system. For instance, a spectrophotometer can include a single two dimensional (2D) array spectrometer or a plurality of linear or 2D array spectrometers, as desired.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to systems and methods for examining spectral data over the course of a high speed event. The systems and methods can enable observation of the spectral evolution of a transient phenomenon into segment intervals on the order of, e.g., milliseconds or microseconds. For example, each time segment interval can be about 50 ms or less, about 20 ms or less about 10 ms or less or even shorter in some embodiments such as about 500 µs, about 100 µs or less, or about 50 µs or less. As such, the systems and methods can be useful in a wide variety of applications such as, and without limitation to, applications involving the formation or use of plasmas, e.g., LIBS applications; examination of high energy devices such as explosions or simulations of explosions; examination of deposition processes, e.g., coating formations; examination of chemical reactions; etc.

Figure 1:
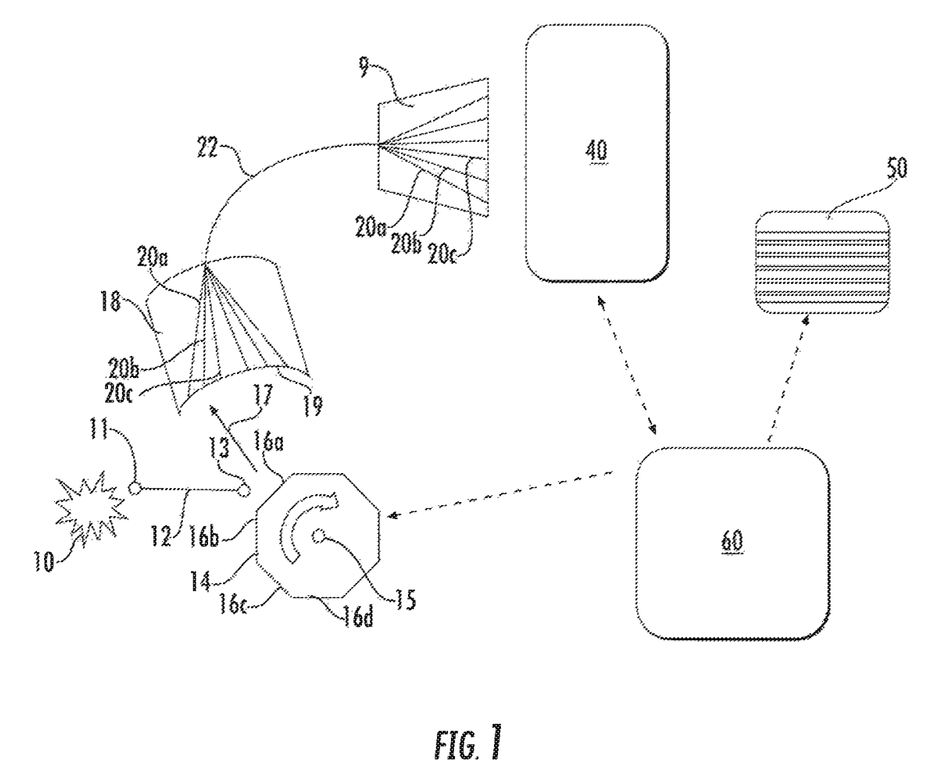
FIG. 1 illustrates one embodiment of a spectroscopy system as disclosed herein.

One embodiment of a high speed spectroscopy system is illustrated in FIG. 1. The system is designed to provide temporal examination of a high speed event that takes place over a period of time at a designated location 10. A high speed event can be, e.g., a laser-induced sample excitation. The entire time period of interest can be, e.g., on the order of about 1 second or less, for instance on the order of milliseconds. By use of the system, data from the event at location 10 can be collected in a plurality of smaller time segments over the course of the entire time period of interest. For instance the time period of interest can be broken into segments on the order of milliseconds, microseconds, or even smaller in some embodiments, and spectral data can be obtained from each segment by use of the system.

As an event proceeds through time, light caused by the event at the location 10 can travel to a rotatable mirror 14. As utilized herein, the term "light" generally refers to electromagnetic energy falling anywhere within the ultra violet/visible/infrared spectrum (UV/Vis/IR), i.e., generally from about 10 nanometers (nm) in wavelength to about 100 micrometers (µm) in wavelength. The collected and examined light from an event can include all or a portion of a spectrum within this range. For instance, a method can include collection and analysis of only the UV portion of light emitted from an event, only the visible portion, only the near IR portion, only the total IR portion, or any combination thereof, as desired.

While the light can be allowed to simply travel through free space from the location 10 to the rotatable mirror 14, in some embodiments it may be preferred to capture, collect and control light from the event for delivery to the mirror 14. For instance, light from the event can be collimated and concentrated by use of a suitable optical waveguide system 12 as is known in the art. For example, light from the event can be collimated and collected for optical communication from the location 10 to the mirror 14 by use of a collimating lens 11 as is known. Examples of suitable collimating lenses can include, without limitation, a cylindrically-shaped gradient-index (GRIN) lens employing a graduated radial refractive index profile, an axial GRIN lens, a molded polymer or glass lens having a spherical or aspherical lens surface, a composite or complex lens element, or an optical fiber having an integral lens, or a ball lens are examples of many alternatives as are generally known in the art.

A lens 11 can be in optical communication with an optical waveguide 12 that can direct and deliver the collected light to the rotatable mirror 14. Any suitable optical waveguide 12 can be utilized. In general, an optical waveguide 12 can be in the form of an optical fiber, but waveguides are not limited herein to optical fibers. Optical waveguides for use in a system can have a variety of physical characteristics, depending upon the specific requirements of a sensing system and site of inquiry, among other considerations. In general, an optical fiber may include a core, through which light may travel, and an external cladding layer. The difference in the index of refraction between the core material and the clad material defines the critical angle at which total internal reflection takes place at the core/clad interface. Thus, light that impinges upon the interface at an angle greater than the critical angle is completely reflected, allowing the light to propagate down the fiber.

Optical fibers for the disclosed systems may generally include multi-mode fibers having a core diameter greater than about 10 micrometers (µm). The preferred core diameter in any particular embodiment may depend upon the characteristics of the event that provides the light that is expected to travel through the fiber, among other system parameters. For instance, in those embodiments in which a laser excitation event provides the signal through the optical fiber, a core diameter may be between about 50 µm and about 100 µm. In other embodiments, for instance in those embodiments in which an event produces less coherent radiation, it may be preferable to utilize an optical fiber for collecting and communicating the event light from the location 10 to the mirror 14 having a somewhat larger core diameter, for instance between about 90 µm and about 400 µm.

In general, fiber size can be determined by the optical spot size from the mirror 14 and according to the collimation optics used to direct light to mirror. Moreover, the size of the mirror and the distance can allow for relatively large spot sizes and use of a waveguide in the form of a glass rod rather than an optical fiber to collect the temporal event. Optical fibers may be preferred in some embodiments as they are small and easily obtained, flexible, and work well with existing scanner mirrors, but it should be understood that use of optical fibers is not a requirement in disclosed systems and any suitable device including, without limitation, an optical fiber, a glass rod, a telescope, etc. may be used to collect the event signal emissions at or near the location 10 of the event and direct them to the rotating mirror 14.

In those embodiments in which the waveguide 12 incorporates a clad, the core/clad boundary of a waveguide 12 may be abrupt, as in a step-index optical fiber, or may be gradual, as in a graded-index optical fiber. A graded-index fiber may be preferred in some embodiments, as graded index fibers may reduce dispersion of multiple modes traveling through the fiber. This is not a requirement however, and step-index fibers may alternatively be utilized, particularly in those embodiments in which an optical fiber is of a length such that dispersion will not be of great concern.

A waveguide may be formed of suitable materials that may be safely located near an event. For example, an optical fiber formed of any suitable type of glass may be used, including, without limitation, silica glass, fluorozirconate glass, fluoroaluminate glass, any chalcogenide glass, or so forth may form the core and/or the clad. Polymer optical fibers (POF) are also encompassed. For instance, an optical fiber formed of suitable acrylate core/clad combinations, e.g., polymethyl methacrylates, may be utilized. It may be preferred in some embodiments to utilize a multi-core POF for collecting and communicating light from an event 10 to a rotatable mirror 14 so as to lower losses common to POF due to bending of the fiber.

Light from the event can be delivered from the second end 13 of the waveguide 12 to the rotatable mirror 14. The rotatable mirror can have an axis of rotation 15 that is generally normal to the propagation direction of travel of the light as it contacts and is reflected off of a surface of the mirror 14. Thus, light can exit the second end 13 of the optical waveguide 12 and be reflected off of a surface 16a of the mirror and thus redirected to a collector 18 as indicated by the arrow 17 as the mirror 14 rotates about the axis 15.

The rotatable mirror 14 can include a plurality of reflective surfaces 16a, 16b, 16c, 16d, etc. that can provide a substantially continuous spectral emission from the event in a predetermined angular field of view that can encompass the facing surface 19 of the collector 18. However, by use of the rotating mirror 14, the light from the event can be broken into a plurality of spectral emissions, each of which encompasses a temporal window. As such, the system allows the temporal event that takes place at location 10 to be transformed into a spatial distance and thereby broken into a series of separate spectral emissions, each of which covering a segment of the entire event. Moreover, the rotational rate of the mirror can be controlled so as to allow the individual temporal window segments to be adjusted. A slow mirror increases the temporal time window of each spectral emission while a faster mirror can decrease the temporal time window of each spectral emission. In general, the ultimate speed of the window can be limited by the maximum safe rotational rate as well as the size of the optical spot and fibers. By way of example, the rotational rate of the mirror 14 can be from about 0.01 cycles (rotations) per second (Hz) to about 50 kHz, depending upon the characteristics of the event and the information to be obtained from the event. For example a mirror rotating at 10,000 revolutions/sec has a timing sweep limit across one face of an octagonal mirror of 125 microseconds. For a hexagonal mirror it would be 166 microseconds. In a slower rotation of 100 revolution/sec then the sweep times would be 1.25 milliseconds and 1.66 milliseconds, respectively. At one Hertz the sweep times would 125 milliseconds for an octagonal mirror and 166 milliseconds for a hexagonal mirror.

The surfaces 16a, 16b, etc. of the mirror 14 can generally be flat so as to limit distortion of the reflection, and the rotatable mirror 14 can thus be in the form of a polygon. The particular characteristics of the surfaces 16a, 16b, 16c, etc. can vary as is known in the art, generally depending on the particular characteristics of the wavelength(s) of light to be reflected to the collector 18. The number of sides of the polygon is not particularly limited and, while illustrated as an octagon, the mirror 14 is not limited to any particular shape, provided that the path of the beam 17 from the mirror can scan across the facing surface 19 of the collector 18 as it rotates and provide a series of spectral emissions from the event 10 to the collector 18.

The collector 18 can include a plurality of optical waveguides 20a, 20b, etc. that are located such that a first end of each of the optical waveguides is at the facing surface 19 of the collector 18 and are spaced apart from one another across the surface 19. Thus, as the mirror 14 rotates light reflected off of the mirror from the event 10 can scan across the surface 19 and each spectral emission can be collected sequentially by each successive optical waveguide 20a, 20b, 20c. The collector 18 can include any number of individual optical waveguides such as, and without limitation about 3 or more, about 5 or more, about 10 or more, or even greater in some embodiments. The optical waveguides 20a, 20b, 20c, etc. are generally placed on an arc of the rotation beam 17 at an angle to optimize or maximize the light collection efficiency from the reflected light. As such, the waveguide surfaces can be nearly orthogonal to the reflected beam 17, but this is not a requirement of the system.

The system can include one or more lenses to collect and/or integrate light for each of the waveguides 20a, 20b, 20c, etc. In this embodiment each waveguide can collect light over an integral period that can be determined by the size of the collection lens and that can be limited by the space between each waveguide. More collection waveguides 20a, 20b, 20c, etc. can provide a higher temporal resolution but less light collected as the time window narrows.

Figure 2:
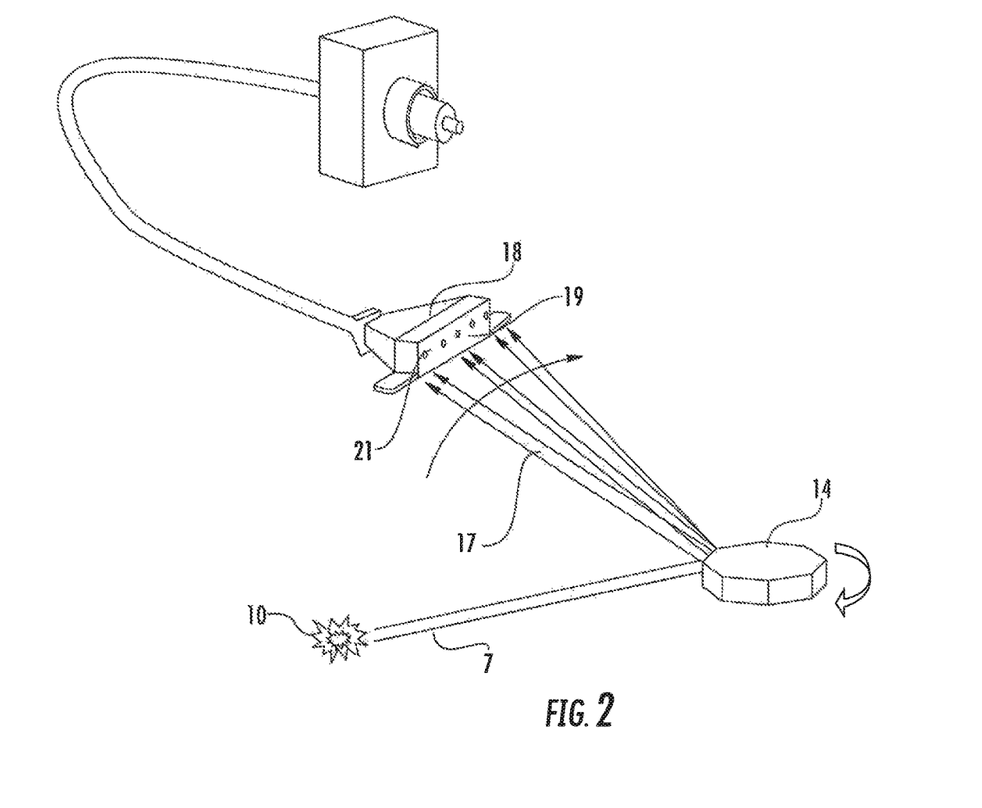
FIG. 2 illustrates a light collection portion of a spectroscopy system as disclosed herein.

A perspective view of this sequential collection process is illustrated in FIG. 2. As shown, the light travels via the path 7 from the event at location 10 to the rotating mirror 14 where it is reflected and thence passes via the rotating beam 17 to the facing surface 19 of the collector 18. Spaced across the facing surface 19 are the collection ends 21 of a series of optical waveguides.

As discussed, the rate of rotation of the mirror 14 in conjunction with the spacing of the collection ends 21 of the waveguides held by the collector 18 and the location of each waveguide collection end 21 with respect to the reflecting surface of the mirror 14 can be varied, depending upon the particular characteristics of a system. Through use of the system, the temporal event at location 10 can be transformed to a spatial distance and thereby a plurality of well-defined spectral emissions from the temporal event can be provided to the waveguides of the collector 18.

Figure 3:
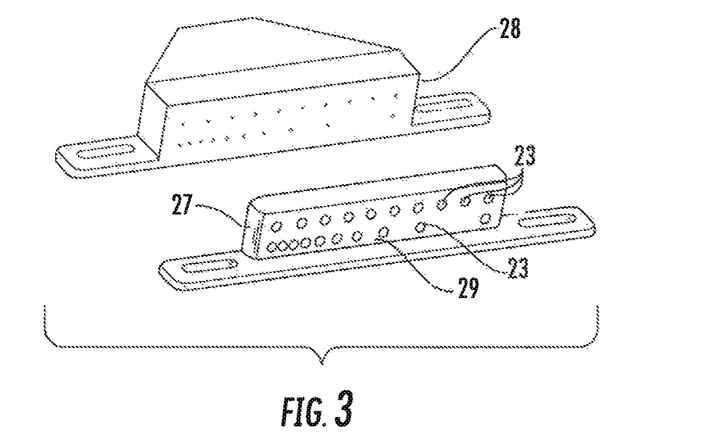
FIG. 3 illustrates a linear log-scale light collector.
Figure 4:
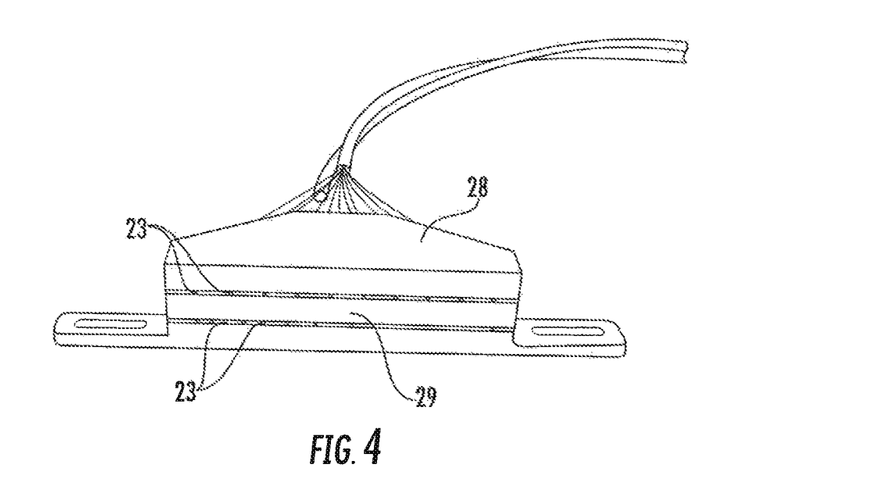
FIG. 4 is a photograph of a linear log-scale light collector.

FIG. 3 and FIG. 4 illustrate one embodiment of a collector 28 for which the facing surface 29 is flat. FIG. 3 illustrates the collector 28 in an exploded view including a bracket 27 that can hold the collection ends of optical waveguides retained by the collector 28. The bracket 27 includes a series of apertures 23 for the collection ends of the optical waveguides to be held by the collector 28. In this particular embodiment, the apertures 23 are arranged in two distinct rows such that the collection ends spaced apart from one another in each row in a logarithmic scale, as indicated by the locations of the apertures 23.

Figure 5:
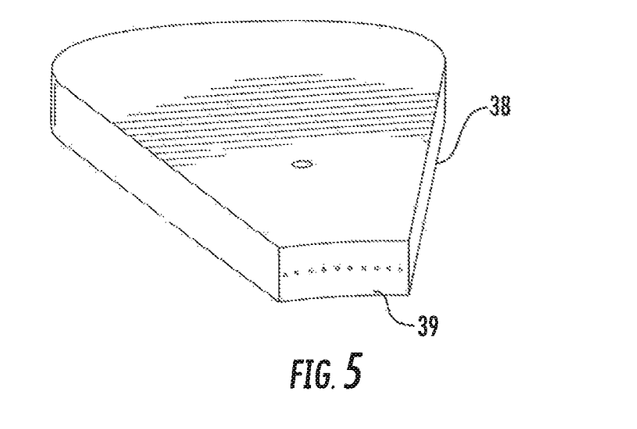
FIG. 5 illustrates a curved surface light collector.
Figure 6:
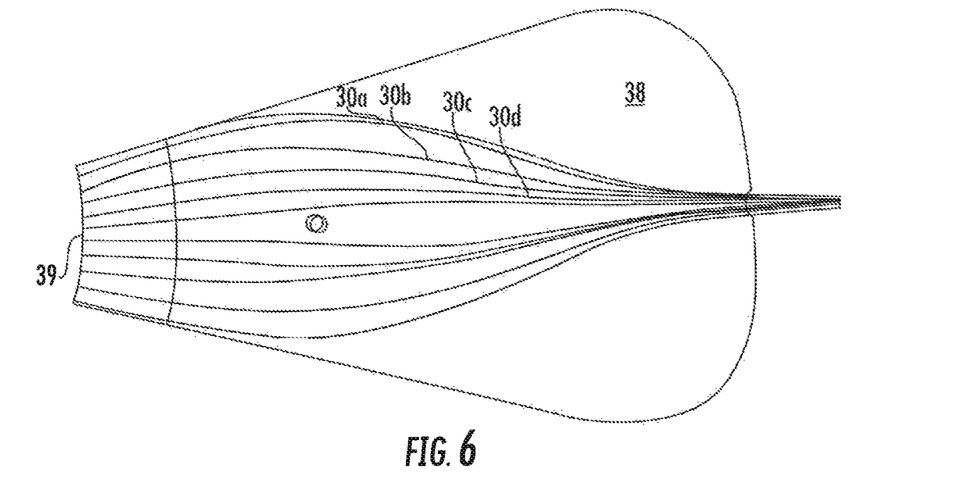
FIG. 6 is a photograph of a curved surface light collector.

In the embodiment of a collector 38 shown in FIG. 5 and FIG. 6, the facing surface 39 of the collector is curved. A curved facing surface 39 can be beneficial in some embodiments, as this geometry can more accurately locate the collection end of each of the optical waveguides 30a, 30b, etc. of the collector 38 at the focal point for the light reflected off of the rotating mirror so as to maximize the light collected from the beam reflected off of the rotatable mirror.

Referring again to FIG. 1, each of the collection waveguides 20a, 20b, 20c, etc. of the collector 18 can generally be held in optical communication with a collection lens held in conjunction with the facing surface 19 of the collector 18. The specific design and geometry of any lens as well as of the optical waveguides themselves can vary as known in the art. Examples of suitable collection lenses and optical waveguides for use in a collector 18 encompass those as described above with regard to the waveguide system 12. While the different optical waveguides 20a, 20b, 20c, etc. of the collector 18 can generally be identical to one another, this is not a requirement of a system. For instance, one or more of the waveguides 20*a*, 20*b*, 20*c*, etc. can include one or more devices such as a filter, polarizer, etc. that can modify or control the light that enters that particular waveguide. In addition, the optical waveguides 20*a*, 20*b*, 20*c*, lenses, etc. of the collector 18 can be the same or different as those used in an optical waveguide system 12 used to communicate light from the event to the rotatable mirror.

As discussed previously, as the mirror 14 rotates, a spectral signal can be conveyed sequentially to each of the optical waveguides 20*a*, 20*b*, 20*c*, etc. A detection process can generally include a single signal to each of the optical waveguides. Thus, a first spectral emission encompassing the first time segment of the time period of interest (e.g., encompassing all or a part of an event) can be delivered to the first waveguide 20*a*. Following, a second spectral emission encompassing the second segment of the time period of interest can be delivered to the second waveguide 20*b*, and so on through the entire scan across the facing surface 19.

There system can also include a rotational position signal from the rotational mirror that can allow the position of the mirror to be synched with a detection shutter and thereby set the collection fiber sequence. The mirror position at the point of an event can be determined so as to determine the initial collection fiber for capturing the spectral emissions of the event as well as to allow collection to be stopped, e.g., after a single sweep of the collection waveguides 20*a*, 20*b*, 20*c*, etc. An event can be initiated randomly and start collection with any waveguide or it can be timed so as to begin in synch with a designated starting position of the mirror 14 and designated initial collection waveguide (e.g., 20*a*). As long as the starting position is known and the fibers are not re-swept during the event, the temporal data can be determined from any starting position.

In one embodiment, the rotatable mirror 14 can include suitable sensor for use in control of the system. For example, The rotatable mirror 14 can include a series of Hall effect magnetic sensors that can enable timing pulses to determine the rotational position of the mirror 14. Optical or other sensors for determining the rotational mirror timing position can alternatively be used. When considering use of logarithmically located collection waveguides as illustrated in FIG. 3 and FIG. 4, it is generally preferable to have the start position of the reflected light (i.e., the mirror) be synched with the initial collection waveguide, but when considering evenly spaced collection waveguides any position can be the starting position.

Referring again to FIG. 1, the individual collection optical waveguides 20*a*, 20*b*, 20*c*, etc. can be combined to form on optical fiber bundle 22 for delivery of the spectral emission carried by each individual waveguide to a spectrophotometer 40. Accordingly, the terminal portion 9 of the collector 18 can deliver the light from each of the optical waveguides 20*a*, 20*b*, 20*c*, etc. sequentially to the spectrophotometer 40 via, e.g., a vertical slit as is known in the art.

The spectrophotometer 40 can be configured to provide a separate spectral output 50 for each signal provided to the spectrophotometer 40 from the individual waveguides 20*a*, 20*b*, 20*c*, etc. The spectrophotometer can thus include one or more diffraction gratings, spectrometers, lenses, beam splitters, and timing circuitry, et etc. as is known in the art. By way of example, a spectrophotometer can include collimating lens at the input of the system (e.g., at the vertical slit), and one or more diffraction gratings downstream of the collimating lens. The diffraction gratings act selectively to respond to the spectral emissions impinging thereon and provide a predetermined angular dispersion of the spectral emissions. In one embodiment, the incoming emissions can be split so as to divide the incoming spectral signal into multiple contiguous bands encompassing different wavelengths, and each of these bands can then be directed to a diffraction grating. For instance, an incoming emission signal can be split and the split signals then directed to a different diffraction grating so as to examine different portions of the incoming signal by use of different detectors specifically designed for that portion (e.g., visible wavelengths in a first continuous band and UV wavelengths in a second contiguous band). The number and bandwidth of each dispersed emission can be selected to maximize the detection threshold, as is known.

Depending upon the characteristics of the system, the spectrophotometer can include a single or multiple detectors (i.e., spectrometers). For instance, in those embodiments in which the time segments for each sequential spectral emission delivered to the spectrophotometer 40 are shorter than the refresh rate of a single detector, the spectrophotometer can include multiple detectors, and sequential spectral signals delivered to the spectrophotometer 40 can be directed to different detectors. In one embodiment, each of the temporal collection fibers 20*a*, 20*b*, 20*c*, etc. can deliver the spectral emission of that fiber to a different spectrometer or alternatively to a single spectrometer with a positional array for stacked temporal spectra display.

A minimum of two dimensional spectral analysis is necessary in a system in order to split two fibers with different spectral content at different times. Thus, an analysis system can generally incorporate a two dimensional spectrometer. While single linear arrays can be utilized in a system, in order to use such, a complex configuration of multiple detectors would be required, which can add both complexity and costs. Beneficially, as the collection waveguides can be arranged in a linear (e.g., vertical) fashion and focused to the slit of the spectrophotometer 40, the light from the fibers can be focused at the detector at different rows of a 2D detector. Each row can then provide a complete spectrum for a given time. By way of example, Row 1 of a 2D detector can provide a spectral emission at time T0, Row 2 emission is at T0+delta T1, Row 3 is T0+delta T3, etc.

The spectral resolution of the system can be determined by the grating resolution and the spectrograph. The temporal resolution of the system can be determined by the rotational speed of the mirror(s) and the separation of the waveguides 20*a*, 20*b*, 20*c*, etc. that sequentially collect the light from the event. The position of the light at the spectrophotometer 40 can be determined by the location of the waveguides with respect to the slit as well as the magnification factor of the spectrophotometer 40 and parameters such as the astigmatism as are known in the art. In general, the maximum number of collection waveguides 20*a*, 20*b*, 20*c*, etc. can be determined by the number of rows in the spectrophotometer 40, although the number can also be determined by the characteristics of the spectrophotometer 40 in order that light from one waveguide can occupy only one row of sensing elements of a detector.

A spectrophotometer 40 may employ photovoltaic or photoconductive detection, depending on the desired spectral response and noise characteristics of a system and an application. Thus, spectrophotometer 40 can provide a spectral output 50 that includes data from each spectral emission delivered to the spectrophotometer 40, each spectral emission describing an emission over a time segment of the total time period of interest. For instance, the spectral output 50 can include data with regard to emission amplitude as a function of wavelength.

Beneficially, a system design can be easily adapted to a specific application from the broadest needs of a wide spectrum (e.g., about 10 nm to about 100 µm) or any portion thereof to examine specific infrared, visible, or ultraviolet wavelengths of interest.

The pixels of a detector can be incrementally spaced in proportion to a given wavelength to which each of the elements is responsive so as to provide a signal representative of a given spectral emission amplitude as a function of wavelength. The diffraction gratings and corresponding detectors can be aligned in cooperation to maintain registration of the angularly disposed spectral emissions with the sensing elements. As is known, the angle of incidence of the gratings defines the angle of dispersion and width of the dispersion field, and this can be optimized to provide registration of the disbursed emissions with the spacing of the detector sensors.

The system can also include a control system 60 configured for signal processing and control. The control system 60 can include electronics and communications software and hardware suitable for data acquisition and processing. For example, outputs of the sensing elements of a detector can be directed to a signal processor of the control system 60 that can include a sample-and-hold circuit for holding a detected signal at a substantially constant value for a predetermined period of time corresponding to the time to scan a pixel, followed by an analog-to-digital converter. Each detector element can be processed in parallel, thereby to provide a continuous signal output in digital form at each of the sensed spectral frequencies for each spectral output 50.

For example, a signal from a detector of the spectrophotometer 40 can be applied to amplifier channels and integrated and applied to an integrator and sample and hold circuit of the control system 60. The integrator and sample and hold circuit can receive control signals from a timing control circuit for procurement of each spectral output 50. The timing control circuit can include an encoder clock signal which has an active low period T1 (e.g., of approximately 1.0 µs) and a quiescent period T2 that can vary with the number of pixels in a scan interval and the scan speed. Typically, with 512 pixels/scan a sample rate can range from about 5 Khz to about 50 Khz in accordance with an optical scan rate of 5 to 50 scans/sec. The interval between encoder clock pulses represents the scan time of one sensing element. Since the detector output is continually varying during the scan cycle, an integrator can provide a continuous output signal that is incremented with time. The sample rate then can define an average pixel amplitude and a period controlled by a timing waveform. The sample period can thus be coincident with the encoder clock frequency. Analog-to-digital conversion can be initiated at the completion of an encoder clock pulse and can be followed by a discharge signal denoted by spectral output 50.

The timing control of a control system 60 can also be in communication with the rotatable mirror 14 so as to control an entire detection cycle over an entire time period of interest as well as to control the acquisition of each individual spectral output 50 over the time period of interest, as discussed above.

A detection cycle can be triggered manually or automatically. For instance, triggering may be from a synchronization pulse from an event 10 that can be timed with the rotational position of the mirror 14. Alternatively, the mirror 14 can be allowed to rotate freely, and triggering of a detection cycle can be tied to detection of a signal on one of the collection fibers (e.g., 20a), which can set a start position for a cycle. A cycle of sequential signals delivered to the spectrophotometer 40 can pass through each of the following fibers (20b, 20c, etc.) as the total signal over the entire time period of interest progresses through all of the fibers. Optionally, if an event repeats, multiple collections could be added to improve the signal to noise ratio compared to a single event.

It may be seen that the present systems and methods can provide a great deal of spectral information for a high speed event of interest.

While certain embodiments of the disclosed subject matter have been described using specific terms, such description is for illustrative purposes only, and it is to be understood that changes and variations may be made without departing from the spirit or scope of the subject matter.

What is claimed is:

1. A spectroscopy system comprising:
a rotatable mirror comprising a surface that is configured for location in optical communication with an event;
a collector in optical communication with the rotatable mirror, the collector comprising a facing surface and a terminal portion, the collector being located such that light from an event is reflected off of the rotatable mirror and thence directly to the facing surface of the collector, the collector comprising a plurality of optical waveguides, each of the optical waveguides comprising a first end and a second end, each of the optical waveguides comprising a collection lens at the first end, the collection lenses being located in series across the facing surface of the collector, the terminal portion of the collector comprising the second end of each of the optical waveguides, the second ends being located in series across the terminal portion; and
a spectrophotometer comprising at least one detector, the spectrophotometer being in optical communication with the terminal portion of the collector such that light that exits each of the optical waveguides via the second end of the optical waveguides is communicated to the spectrophotometer.

2. The spectroscopy system of claim 1, wherein the rotatable mirror comprises a plurality of reflective faces.

3. The spectroscopy system of claim 1, further comprising a waveguide system in optical communication with the rotatable system and configured to carry light from the event to the rotatable mirror.

4. The spectroscopy system of claim 1, the optical waveguides comprising optical fibers.

5. The spectroscopy system of claim 4, wherein the optical fibers comprise multi-mode optical fibers.

6. The spectroscopy system of claim 1, the spectrophotometer comprising multiple detectors.

7. The spectroscopy system of claim 1, wherein the detector comprises a two dimensional array of sensing elements.

8. The spectroscopy system of claim 1, the facing surface defining a curve.

9. A method for examining a high speed event comprising:
locating a rotatable mirror in optical communication with the high speed event such that for a first time segment light from the event is reflected off of the rotatable mirror and thence directed from the mirror directly to a facing surface of a collector, the collector comprising a plurality of optical waveguides, each of the optical waveguides comprising a first end and a second end, each of the optical waveguides comprising a collection lens at the first end, the collection lenses being located in series across the facing surface of the collector, a terminal portion of the collector comprising the second end of each of the optical waveguides, the second ends being located in series across the terminal portion, the light of the first time segment being directed from the mirror to a collecting lens of a first optical waveguide that is one of the plurality of optical waveguides of the collector, the first optical waveguide collecting the light of the first time segment as a first spectral signal;

rotating the mirror such that for a second time segment following the first time segment light from the event is reflected off of the rotatable mirror and thence directed from the mirror directly to a collecting lens of a second optical waveguide that is one of the plurality of the optical waveguides of the collector, the second optical waveguide collecting the light of the second time segment as a second spectral signal;

the first spectral signal traveling along the first optical waveguide, exiting the second end of the first optical waveguide, and thereafter being detected by a detector of a spectrophotometer;

the second spectral signal traveling along the second optical waveguide, exiting the second end of the second optical waveguide, and thereafter being detected by the detector of the spectrophotometer; and the spectrophotometer thereafter carrying out a spectral analysis for each of the first and second spectral signals.

10. The method of claim 9, wherein the high speed event takes place over a period of time of about 1 second or less.

11. The method of claim 9, wherein the event comprises formation of a plasma.

12. The method of claim 11, wherein the plasma is a laser-induced plasma.

13. The method of claim 9, the spectral analysis comprising distributing the first spectral signal across a first array of sensing elements of the spectrophotometer.

14. The method of claim 13, the spectral analysis further comprising distributing the second spectral signal across a second array of sensing elements of the spectrophotometer.

15. The method of claim 14, wherein the first array of sensing elements comprises a two dimensional array of sensing elements.

16. The method of claim 13, further comprising rotating the mirror such that for one or more additional time segments sequentially following the second time segment, light from the event is reflected off of the rotatable mirror and thence directed from the mirror sequentially to one or more additional collecting lens of one or more additional optical waveguides of the collector, the one or more additional optical waveguides sequentially collecting the light from each of the one or more additional time segments as one or more additional spectral signals.

* * * * *